United States Patent

Reents, Jr.

[11] Patent Number: 5,631,462
[45] Date of Patent: May 20, 1997

[54] LASER-ASSISTED PARTICLE ANALYSIS

[75] Inventor: William D. Reents, Jr., Middlesex, N.J.

[73] Assignee: Lucent Technologies Inc., Murray Hill, N.J.

[21] Appl. No.: 373,732

[22] Filed: Jan. 17, 1995

[51] Int. Cl.$^6$ .............................. B01D 59/44; H01J 49/00
[52] U.S. Cl. ............... 250/288; 250/282; 250/287; 250/423 P
[58] Field of Search .................................. 250/281, 282, 250/287, 288, 423 P

[56] References Cited

U.S. PATENT DOCUMENTS

| | | | |
|---|---|---|---|
| 4,383,171 | 5/1983 | Sinha et al. | 250/423 P |
| 4,433,241 | 2/1984 | Boesl et al. | 250/423 P |
| 4,894,511 | 1/1990 | Caledonia et al. | 250/423 P |
| 5,122,752 | 6/1992 | Koga et al. | 250/283 |
| 5,164,592 | 11/1992 | Kitamori et al. | 250/281 |
| 5,365,063 | 11/1994 | Kaesdorf et al. | 250/282 |
| 5,382,794 | 1/1995 | Downey et al. | 250/288 |

Primary Examiner—Bruce C. Anderson
Attorney, Agent, or Firm—Richard J. Botos

[57] ABSTRACT

The present invention provides methods and apparatus for analyzing the particulate contents of a sample such that a high proportion of the sample particles are analyzed without discrimination against high electronegativity and high ionization potential elements. In an exemplary embodiment, the invention comprises an apparatus for analyzing the particulate content of a sample having particulate diameters in range of 0.001–10 microns. The apparatus comprises an evacuable chamber equipped with a chamber entrance through which a particle-laden gas stream enters. An inlet device, such as a capillary, communicates with the chamber entrance for inputting the particle-laden gas stream to the evacuable chamber. A laser is positioned to produce a focused laser beam which intersects the particle-laden gas stream at a position approximately 0.1 mm from the chamber entrance. The laser beam has a power density sufficient to fragment and ionize particles entrained within the particle-laden gas stream. A detector is positioned to detect the ionized species produced by the laser.

14 Claims, 2 Drawing Sheets

LASER-ASSISTED PARTICLE ANALYSIS

FIELD OF THE INVENTION

The present invention relates to laser-assisted particle analysis and, more particularly, to laser-assisted spectrometry systems for analyzing particulate-laden gas streams.

BACKGROUND OF THE INVENTION

Particle detection and analysis is desirable in a variety of manufacturing and environmental contexts. For example, in clean rooms used for the fabrication of integrated circuits, highly accurate particle detection is required due to the small dimensions of the devices under production. Significant failure rates in integrated circuits are associated with the presence of particles greater than one-tenth the device linewidth. Typically, the smaller the size of the particle, the greater the number of particles which are present. Therefore, as linewidths decrease within the sub-micron range, particle removal becomes increasingly difficult and costly. Consequently, control of a particle source is usually more cost-effective than removal of particles once they are liberated from their source. Through real-time particle analysis, particle sources can be identified and controlled.

Particle detection and analysis in clean rooms and gas distribution systems is typically done by real-time, also known as on-line, counting of airborne particles followed by off-line analysis of deposited particles by microscopic or laser scan techniques. The former technique provides the rapid response required for monitoring particle generation events while the latter technique provides size and elemental composition information. Particle counting is frequently performed using standard light-scattering particle counters. However, these devices can only detect particles on the order of 50 nanometers or greater and provide no compositional information. While off-line analysis provides particle composition information, it is also limited by the particle sizes it can detect and cannot be time-correlated to particle generation events.

Mass spectrometry is an analytical technique used for the accurate determination of molecular weights, identification of chemical structures, determination of mixture compositions, and quantitative elemental analysis. Molecular structure is typically determined from the fragmentation pattern of ions formed when the molecule is ionized. Elemental content of molecules is determined from mass values obtained using mass spectrometers. However, since mass spectrometers typically operate in vacuum, particulate analysis usually requires that nearly all of the particulate carrier be separated from the particulate material prior to ionization in the spectrometer. This requirement increases the complexity of particle detection for particulates suspended in liquids and gases.

Real-time or on-line particle analysis for particles suspended in gases is normally accomplished by sampling particles through a differentially pumped nozzle and impacting the particle beam onto a heated surface. In this manner, impinging particles are ionized and analyzed. However, this surface ionization technique results in the creation of ions from both the particle beam and the surface being heated, making it difficult to determine the composition and size of the particles of interest. Additionally, not all elements of the particulate sample will form ions, resulting in discrimination against certain elements, typically those elements with high electronegativities and high ionization potentials.

More universal detection can be achieved through electron impact ionization of neutral species ejected by the collision of a particle beam with a heated surface. However, this method creates extensive fragmentation and results in lower ionization yields than surface ionization. Scanning mass analyzers, such as the quadrapole or magnetic sector analyzers can also be used for particulate analysis. Due to the transient nature of the signal produced in these devices, it is difficult or impossible to obtain a complete mass spectrum. As a result, these analyzers show poor sensitivity and difficulty in performing multicomponent determinations.

Many of the difficulties associated with the above techniques can be reduced or eliminated through the use of a laser-induced mass spectrometry system taught in U.S. Pat. No. 5,382,794 issued Jan. 17, 1995, commonly assigned to the instant assignee, the disclosure of which is incorporated by reference herein. In the patent, an exemplary laser-induced mass spectrometry system is described in which particles enter an evacuable chamber through an inlet device such as a capillary. A laser, such as a pulsed laser, is positioned such that the laser beam intersects the particle stream. As the particles pass through the path of the laser beam, they are fragmented and ionized. A detector, such as a time-of-flight mass spectrometer detects the ionized species. Mass spectra are produced, typically being recorded with an oscilloscope, and analyzed with a microprocessor. The mass spectra information permits real-time analysis of the particle size and composition.

While the laser-assisted spectrometry system described in the patent provides useful real-time particulate analysis, there is a continuing need to provide compositional and size evaluation for increasingly smaller particulates. There is a further need in the art for detection and analysis of a greater percentage of the particulate contents of a sample, to ensure accurate characterization. Finally, there is a need in the art for particulate analysis systems and techniques which do not discriminate against high electronegativity and high ionization potential elements.

SUMMARY OF THE INVENTION

The present invention provides methods and apparatus for analyzing the particulate contents of a sample such that a high proportion of the sample particles are analyzed without discrimination against high electronegativity and high ionization potential elements. In an exemplary embodiment, the invention comprises an apparatus for analyzing the particulate content of a sample having particulate diameters in a range of 0.001–10 microns. The apparatus comprises an evacuable chamber equipped with a chamber entrance through which a particle-laden gas stream enters. An inlet device, such as a capillary, communicates with the chamber entrance for inputting the particle-laden gas stream to the evacuable chamber. A laser is positioned to produce a focused laser beam which intersects the particle-laden gas stream at a position approximately 0.05 mm to 1.0 mm from the chamber entrance. The laser beam has a power density sufficient to fragment and ionize particles entrained within the particle-laden gas stream. A detector is positioned to detect the ionized species produced by the laser.

In an exemplary embodiment, the capillary dimensions are selected such that the gas flow is less than approximately 2 milliliters/second and the laser beam has a high power density, typically greater than $10^{11}$ W/cm$^2$. These conditions help ensure accurate detection of a large percentage of the particles entrained in a gas stream, typically on the order of 1 in 100 particles.

DETAILED DESCRIPTION

Figure 1:
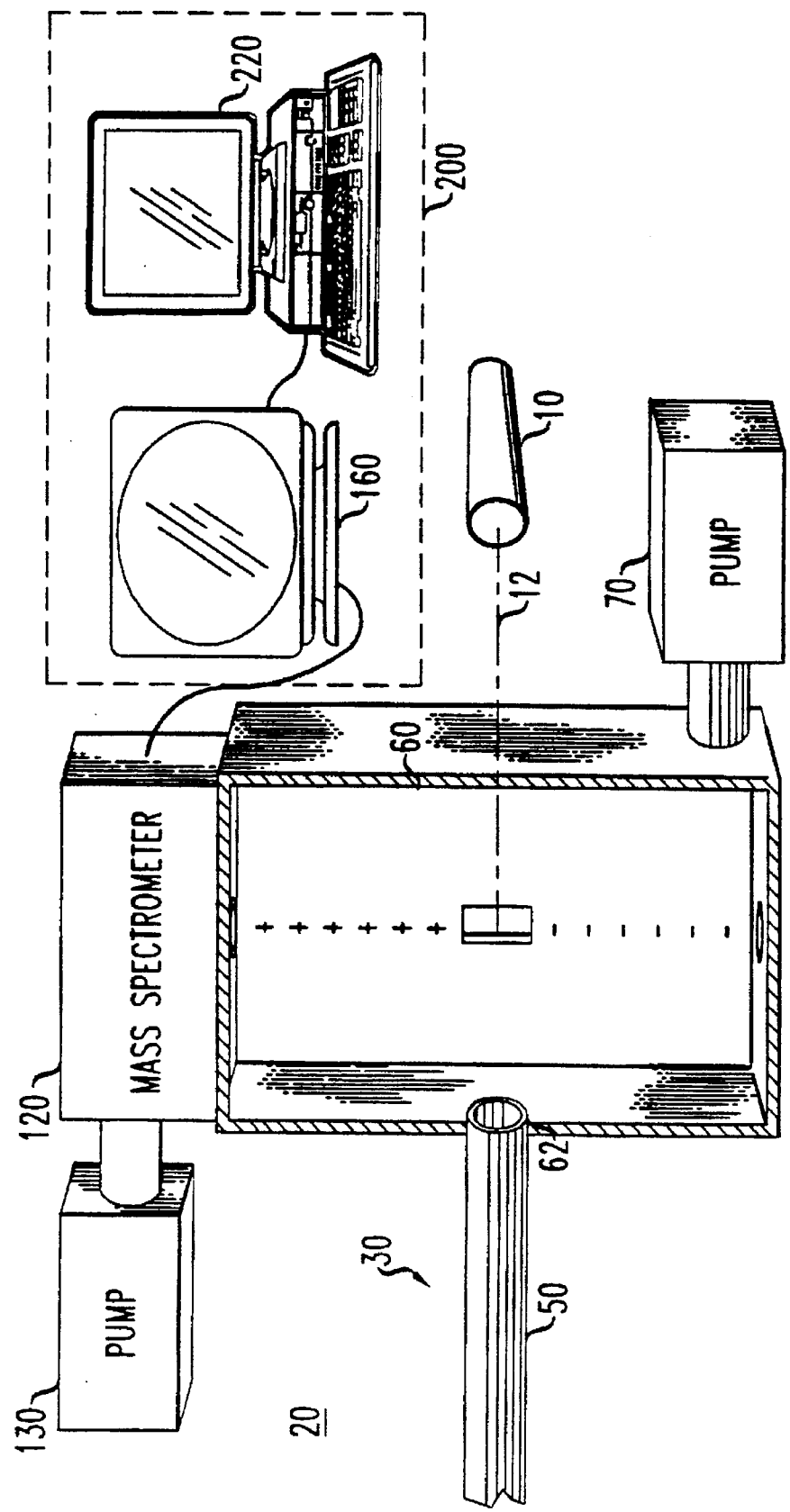
FIG. 1 schematically depicts a laser particle analyzer in partial cross-section according to one embodiment of the present invention.

Referring now to the drawings in detail in which like numerals indicate the same or similar elements in view, FIG. 1 depicts a particle analyzer 20 according to the present invention. The apparatus 20 incudes an inlet device 30 through which particles enter a differentially pumped chamber 60. Chamber 60 is generally maintained at a pressure of at least approximately $10^{-3}$ torr by a vacuum pumping system 70. Pumping system 70 is selected from any device capable of maintaining vacuum in the desired range, including, but not limited to, mechanical pumps, diffusion pumps, cryogenic pumps, turbomolecular pumps, and combinations thereof.

Inlet device 30 includes capillary 50 fabricated from materials which provide a smooth interior surface, such as fused silica. Typically, the inner diameter of inlet device 30 is on the order of 0.20 to 0.53 mm with a length of approximately 0.1 to 10 meters for particle analysis in the submicron range. The use of an inlet capillary of these dimensions assists in collimating the particle-laden gas stream and advantageously eliminates the need for mechanical pumping along the path of the capillary. Further, the small capillary size greatly reduces the velocity of the particle-laden gas stream. As a result of the slower gas stream speed, there is a higher probability that a given particle will reside in a laser spot during a laser pulse; resulting in a higher percentage of particles being analyzed. The volume of particle-laden gas flow is typically less than about 2 milliliters/second. The reduced gas stream velocity also reduces the gas load on the pumping system for chamber 60, permitting use of smaller pumping systems or using pumping system 70 for plural pumping functions.

Figure 2:
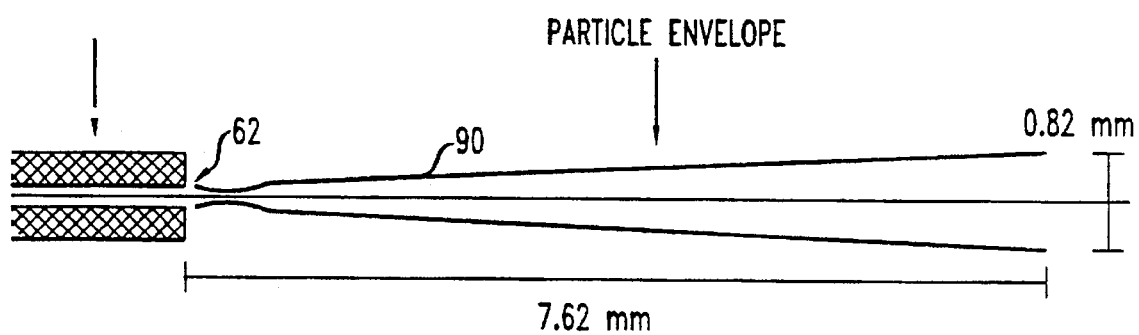
FIG. 2 schematically depicts the particle dispersion from a particle-laden gas stream exiting a capillary.

To ionize the particles injected through capillary 50, a laser 10 is positioned such that the focused laser beam passes through an opening in chamber 60 and intersects the particle-laden gas stream adjacent chamber entrance 62. In a preferred embodiment, the edge of the beam spot is positioned on the order 0.05–1.0 mm from the chamber entrance. In an exemplary embodiment, the beam edge is positioned 0.1 mm from the chamber entrance. As depicted in FIG. 2, the particle-laden gas stream 90 begins to disperse immediately upon entering chamber 90. As a result of this dispersion, the further away from chamber entrance 62 that the laser beam 12 intersects particle-laden gas stream 90, the smaller is the subtended angle of the dispersion. Further, smaller particles are more easily carried by the expanding gas to a larger radius, while larger particles, e.g., particles greater than one micron, are concentrated in the center of the particle stream. As a result, positioning the focal point of the laser beam beyond the chamber entrance will tend to discriminate more heavily against analysis of smaller sized particulates. Consequently, a smaller percentage of the total number of particulates is ionized and analyzed for laser/gas stream intersection at any appreciable distance beyond chamber entrance 62. For the described configuration of the FIG. 1 analyzer, approximately 1 out of every 100 particles is analyzed.

In one embodiment, the desired spatial relationship among capillary 50, chamber entrance 62, and laser beam 12, is created through use of a precision x-y-z manipulator (not shown). It is emphasized that use of an x-y-z manipulator is illustrative. Any arrangement, adjustable, or fixed, which ensures the proper spatial relationship among these components can be used with the particle analyzers of the present invention. Capillary 50 is positioned within the manipulator and set to the desired distance from the laser beam.

The vibrations of the capillary are damped by an external fixed arm (not shown) so that the position of the capillary with respect to the laser beam can be maintained despite vibrations. The vibration damping element is a fixed arm which extends in one of the perpendicular directions Laser 10 is selected from pulsed lasers having a short pulse width, a high peak power, a moderate spot size, and a high repetition rate. For the embodiment shown in FIG. 1, laser 10 has a pulse frequency in the range of 10 Hz to 10 kHz with a frequency of from 1 to 10 kHz being exemplary. The laser power is at least approximately 0.5 mJ with a power density on the order of at least $1.0 \times 10^{11}$ W/cm$^2$ with power densities of greater than $1.0 \times 10^{12}$ W/cm$^2$, and, more particularly, greater than $1.0 \times 10^{13}$ W/cm$^2$, being exemplary. Laser spot sizes are determined by the selected laser power and power density. Typically, laser spot sizes range between 0.001 to 20 mm$^2$.

The use of high laser power densities ensures the ability to fully characterize the particle-laden gas stream. High laser power densities ensure ionization of high ionization potential elements. Additionally, smaller particles, which are more difficult to ionize since they transfer heat more efficiently than larger particles, ionize more readily at the higher laser power densities used in the present invention. Acceptable commercially-available lasers include a Lambda Physik excimer laser, model EMG 202, and a Spectra Physics DCR II Neodymium YAG laser.

Upon introduction of the particle-laden gas stream 90 into capillary 50, laser 10 is turned on and continuously fired. As the particle-laden gas stream enters chamber 60, it passes through the laser beam. The laser beam fragments a particle and ionizes the fragments, forming a plasma. For the high power densities of the present invention, the particle fragments yield positive ions.

A time-of-flight mass spectrometer (TOF/MS) 120, particularly a time-of-flight mass spectrometer including a reflectron, obtains the mass spectra ed by particles ionized by laser 10. While a time-of-flight mass spectrometer is depicted in FIG. 1, it is understood that this spectrometer is illustrative. A variety of mass spectrometers can be employed in the particle analyzers of the present invention including, but not limited to, quadrapole, magnetic sector, and quadrapole ion trap spectrometers, and Penning ion trap spectrometers such as FTICR spectrometers. Time-of-flight mass spectrometer 120 is a positive time-of-flight mass spectrometer. Pump system communicates with the spectrometer to maintain a pressure of less than approximately $10^{-4}$ torr. Optionally, pump system 130 is combined with pump system 70 through a plural port system, reducing the number of pumping elements and hence the overall size and cost of the system.

Due to the high laser power densities employed in the present invention, the ionized particle fragments in the plasma are positive species The spectrometer counts each fragmentation incident and measures the masses and yields of the positive ions produced when the particle contacts the laser beam. The mass of the ions correlates to the travel time required for the ionized particle fragment to contact the mass spectrometer. A Jordan Associates dual time-of-flight mass spectrometer can be employed as spectrometer 12. Optionally, a positively charged grid (not shown) is positioned opposite spectrometer 120 to accelerate the positively charged ions toward the spectrometer.

Information from the spectrometer is transmitted to recording portion 200. In an exemplary embodiment, recording portion 200 comprises a transient recorder 160, such as a digital oscilloscope, which records the mass spectra. Processor 220, such as a computer, analyzes and displays the information received from oscilloscope 160. Optionally, the processor is itself included in recorder 160. It is understood that recording portion 200 is exemplary and that any device capable of recording, displaying, or otherwise processing information from spectrometer 120 is employable as element 200.

The apparatus and methods of the present invention are able to detect very small particles, such as those with a diameter of less than about 0.03 micron. These very small particles produce a small number of ions. This small number results in a low ion density which reduces ion spreading during their flight time. Reduced ion spreading significantly contributes to a reduction in the mass resolution of the time-of-flight mass spectrometer. The mass resolution relates to the width of the arrival time of ions with the same mass. Also, particle fragmentation and ionization time must be short; high laser power densities facilitate particle fragmentation and ionization in time periods less than the laser time width.

Ions from these very small particles produce pulse widths of less than 2 nanoseconds. For the above-described system, an ultrahigh mass resolution of greater than 30,000 at ion mass 180 is achieved. Currently, such resolutions are attained only by massive, costly, magnet-based mass spectrometers. The ability to achieve these resolutions with time-of-flight mass spectrometers represents a considerable cost and size reduction over prior art systems.

Advantageously, the laser-assisted particle analyzers of the present invention substantially completely fragment and ionize the incident particles due to high laser power density. In contrast, low power densities do not completely ionize fragments, so complete particle information is not obtained. By completely fragmenting and ionizing an incident particle, the ionized fragments yield an accurate representation of the parent particle. Consequently, ion measurements yield the amount of particular elements in the particle and the mass of material present in the particle can be directly determined from ion intensities. Other particle techniques typically determine a particle diameter and assume an ideal spherical shape. Mass is derived from the assumed shape using an estimated density. This approximation is especially poor for irregularly-shaped particles and those particles which are porous.

The present invention permits real-time detection and analysis of particles. Real-time analysis is particularly useful for evaluation of particles whose existence is transitory. For example, mechanical devices, when moved, generate a burst of particles for only a short time. Gas transport through a conduit can cause particles to be shed from inner surfaces, especially during pressure changes. Evaluating the composition of these particles, especially those smaller than 0.1 micron in diameter, is made possible through the apparatus and techniques of the present invention. Additionally the present invention is useful for the analysis of the particulate contents of liquid samples, as disclosed in copending U.S. patent application Ser. No. 08/373,731 filed concurrently herewith, and assigned to the instant assignee, the disclosure of which is incorporated by reference herein.

While the foregoing invention has been described in terms of the exemplary embodiments, it will be readily apparent that numerous modifications and changes can be made. Accordingly, modifications such as those suggested above, but not limited thereto, are considered to be within the scope of the claimed invention.

What is claimed is:

1. Apparatus for analyzing the particulate content of a sample, the sample particulates having a diameter in a range of 0.001–10 microns, the apparatus comprising:
   an evacuable chamber, the evacuable chamber including a chamber entrance through which a particle-laden gas stream enters;
   an inlet device communicating with the chamber entrance for inputting the particle-laden gas stream to the evacuable chamber at a velocity of less than about 64 m/sec.;
   a laser positioned to produce a focused laser beam which intersects the particle-laden gas stream at a position approximately 0.1 mm from the chamber entrance, the laser beam having a power density sufficient to fragment and ionize particles entrained within the particle-laden gas stream; and
   a detector positioned to detect ionized species produced by the laser.

2. Apparatus for analyzing the particulate content of a sample according to claim 1 wherein the inlet device is a small diameter capillary.

3. Apparatus for analyzing the particulate content of a sample according to claim 2 wherein the small diameter capillary has a diameter of approximately 0.20–0.53 mm and a length on the order of 0.1–10 meters.

4. Apparatus for analyzing the particulate content of a sample according to claim 1 further comprising a precision x-y-z manipulator supporting the capillary for maintaining the focused laser beam at a position approximately 0.1 mm from the chamber entrance.

5. Apparatus for analyzing the particulate content of a sample according to claim 1 wherein the laser has a power density of at least $10^{11}$ W/cm$^2$.

6. Apparatus for analyzing the particulate content of a sample according to claim 1 wherein the laser has a power density of at least $10^{12}$ W/cm$^2$.

7. Apparatus for analyzing the particulate content of a sample according to claim 1 wherein the laser has a power density of at least $10^{13}$ W/cm$^2$.

8. Apparatus for analyzing the particulate content of a sample according to claim 1 wherein the detector comprises a mass spectrometer.

9. Apparatus for analyzing the particulate content of a sample according to claim 8 wherein the mass spectrometer comprises a time-of-flight spectrometer.

10. A method for analyzing the particulate content of a sample, the sample particulates having a diameter in a range of 0.001–10 microns, the method comprising:
    inputting a particle-laden gas stream through an inlet device at a velocity of less than about 64 m/sec. into an evacuable chamber through a chamber entrance;

focusing a high power density laser to produce a focused laser beam which intersects the particle-laden gas stream at a position approximately 0.1 mm from the chamber entrance, the laser beam having a power density sufficient to fragment and ionize particles entrained within the particle-laden gas stream;

fragmenting and ionizing particles entrained within the particle-laden gas stream; and detecting ionized species produced by the laser interaction with the particle-laden gas stream.

11. A method for analyzing the particulate content of a sample according to claim 10 wherein the detecting is performed using a time-of-flight mass spectrometer.

12. A method for analyzing the particulate content of a sample according to claim 10 wherein the inlet device comprises a capillary.

13. A method for analyzing the particulate content of a sample according to claim 10 wherein the laser has a power density of at least $10^{11}$ W/cm$^2$.

14. A method for analyzing the particulate content of a sample, the sample particulates having a diameter in a range of 0.001–10 microns, the method comprising:

inputting a particle-laden gas stream through an inlet device into an evacuable chamber at a velocity of less than about 64 m/sec. through a chamber entrance;

focusing a high power density laser to produce a focused laser beam which intersects the particle-laden gas stream in the evacuable chamber, the laser beam having a power density sufficient to fragment and ionize particles entrained within the particle-laden gas stream;

substantially completely fragmenting and ionizing incident particles from the particle-laden gas stream; and detecting ionized species produced by the laser interaction with the particle-laden gas stream to directly yield mass and/or compositional data about a particle.

* * * * *